United States Patent
Nguyen

(10) Patent No.: US 10,641,752 B2
(45) Date of Patent: May 5, 2020

(54) DETECTION OF NITROGEN CONTAINING AND NITROGEN FREE EXPLOSIVES

(71) Applicant: SCINTREX TRACE CORPORATION, Ottowa (CA)

(72) Inventor: Dao Hinh Nguyen, Ottowa (CA)

(73) Assignee: SCINTREX TRACE CORPORATION, Ottowa, Ontario (CA)

( * ) Notice: Subject to any disclaimer, the term of this patent is extended or adjusted under 35 U.S.C. 154(b) by 211 days.

(21) Appl. No.: 15/608,911

(22) Filed: May 30, 2017

(65) Prior Publication Data

US 2018/0348184 A1    Dec. 6, 2018

(51) Int. Cl.
| | | |
|---|---|---|
| G01N 33/00 | (2006.01) | |
| G01N 21/76 | (2006.01) | |
| G01N 27/12 | (2006.01) | |

(52) U.S. Cl.
CPC ....... *G01N 33/0037* (2013.01); *G01N 21/766* (2013.01); *G01N 27/125* (2013.01); *G01N 33/004* (2013.01); *G01N 33/0031* (2013.01)

(58) Field of Classification Search
CPC ................................................ G01N 33/0037
USPC ........................................................ 422/940
See application file for complete search history.

(56) References Cited

U.S. PATENT DOCUMENTS

| | | | |
|---|---|---|---|
| 5,395,589 A | 3/1995 | Nacson | 422/88 |
| 6,946,300 B2 | 9/2005 | Nguyen | 436/110 |
| 6,984,524 B2 | 1/2006 | Nguyen et al. | 436/107 |
| 2006/0081073 A1* | 4/2006 | Vandrish | G01N 1/2202 73/864.33 |
| 2009/0131248 A1* | 5/2009 | Bradley | B01D 53/885 502/200 |

OTHER PUBLICATIONS

Danling Wang, "Trace Explosive Sensor Devices Based on Semiconductor Nanomaterials," A dissertation submitted to the University of Washington in 2014.
Yun Chu, "Solid State Gas Sensors for Detection of Explosives and Explosive Precursors," A dissertation submitted to the University of Rhode Island on Jan. 1, 2013.
(Continued)

*Primary Examiner* — Christopher Adam Hixson
*Assistant Examiner* — Emily R. Berkeley
(74) *Attorney, Agent, or Firm* — Ernest D. Buff & Associates, LLC; Ernest D. Buff; Dave Narasimhan

(57) ABSTRACT

A compact explosive detecting system collects explosive residues in the form of vapor powder. The residues are accumulated on a desorber which is subjected to pyrolysis to release a gaseous sample. The sample is pumped to a detecting system through a metering valve. A luminol cell reacts with the gaseous sample to create chemiluminescence, the light output of which is measured by a photo multiplier tube. The light intensity is indicative of the amount of explosive present. Based on the amount of explosive present, a metering valve is adjusted to pass the gaseous sample into a highly sensitive metal oxide sensor array to detect $NO_2$ from nitrogen containing explosive and $CO/CO_2$ from non nitrogen containing explosive. The metal oxide sensor array reliably selects explosives from those compounds indicating chemiluminescence.

10 Claims, 12 Drawing Sheets

(56) References Cited

OTHER PUBLICATIONS

Publication by Prabakaran Shanka et al. ScienceJet, vol. 4: p. 126 "Gas sensing mechanism of metal oxides: The role of ambient atmosphere, type of semiconductor and gases—a review".

Maria Monterola laser photo fragmentation and heterogeneous chemiluminescence for nitrogen-based explosive detection. 2007 Ph.D. Thesis submitted to University of Florida.

Beata Zakrzewska, "Very Sensitive Optical System with the Concentration and Decomposition Unit for Explosive Trace Detection." Published in Metrology and Measurement Systems, vol. XXII (2015), No. 1, pp. 101-110.

Jimmie C. Oxley, "Decompostion of a Multi-Peroxidic Compound: Triacetone-Triperoxide (TATP)." Published in Propellants, Explosives, Pyrotechnics 27, 209-216 (2002). Chemstry Department University of Rhode Island.

* cited by examiner

DETECTION OF NITROGEN CONTAINING AND NITROGEN FREE EXPLOSIVES

BACKGROUND OF THE INVENTION

1. Field of the Invention

This invention relates to the field of scanner apparatus and methods; and more particularly to inspection systems that scan and detect residues of nitrogen containing as well as nitrogen free explosives.

2. Description of the Prior Art

In recent years, the prevalence of criminal activity that entails transportation of explosives used as weapons has been a significant public concern. It has thus become vital to develop systems for detecting the presence of these materials, both when shipped as luggage or cargo and when hand carried by an individual. Of particular concern is the need to detect explosives commonly used as weapons by terrorists, including concealed explosives or incendiary substances, and materials that present hazards to people and property.

The detection of explosives in the context of air and rail transportation is especially challenging, given the need to examine large numbers of people and articles of luggage and cargo within acceptable detection limits on throughput and without excessive intrusiveness. Although physical inspection is a widely practiced and important technique, it is slow, cumbersome, labor intensive, and is dependent on the alertness and vigilance of the inspector.

Automated systems that screen for explosive have been sought for many years. Various techniques have been proposed to detect explosive objects and materials either directly or indirectly.

Vapors from explosives are obtained by using a collection chamber connected to a negative pressure supply such as a pump. The task of indirectly detecting the presence of suspect materials is further complicated by their wide variability in vapor pressure. Some explosives, including nitroglycerin (NG), dynamite, EGDN, and EGTN, are comparatively volatile, exhibiting significant vapor pressure at room temperature. DNT and TNT have lower, but still appreciable room-temperature vapor pressure. However, some of the most critical materials for which detection is sought, e.g. drugs, such as cocaine and heroin, and plastic explosives, such as SEMTEX and C-4, are far less volatile, having room temperature vapor pressures as much as ten million times lower. It is virtually impossible to detect vapor naturally emanating from these low volatility materials. They are even more difficult to detect if sealed inside luggage or packaging.

U.S. Pat. No. 6,946,300 to Nguyen et al. discloses multimodal detection of explosives, narcotics, and other chemical substances. This compact scanning apparatus has an infrared laser adapted to emit light. The light is delivered as a beam by an optical system to illuminate an interrogation area on the surface of an object being scanned to cause selective desorption of molecules of the contraband substance, which are present on the surface, without substantially damaging the surface. A collection system collects at least a portion of the desorbed molecules. At least a portion of the collected molecules is thermally decomposed to form $NO_2$ and transferred to a reaction cell containing an aqueous, alkaline, luminol-containing solution. The $NO_2$ reacts with the luminol to produce light by chemiluminescence. A light detector registers the presence of this light to carry out a rapid screening of the object for the possible presence of the contraband substance. The apparatus further includes a supplemental detector such as a GC/IMS detector that is activated in response to the detection of the chemiluminescent light. The supplemental detector provides confirmation of the detection of contraband substance and activates a signaling device to provide an audible or visible alarm. The rapid pre-screening permits the apparatus to identify suspicious items, while the supplemental detection system can be optimized for more intense, but time-consuming scrutiny of just the suspicious items. Both effective detection and high throughput are thereby achieved in an accurate, reliable manner. This system does not use a MOS detector to detect explosives.

U.S. Pat. No. 6,984,524 to Nguyen et al. discloses chemiluminescent detection of explosives, narcotics, and other chemical substances. This compact scanning apparatus has an infrared laser adapted to emit light. The light is delivered as a beam by an optical system to illuminate an interrogation area on the surface of an object being scanned. Such illumination has sufficient intensity and duration to cause selective desorption of molecules of the contraband substance, which are present on the surface, without substantially damaging the surface. A collection system collects at least a portion of the desorbed molecules. At least a portion of the collected molecules is thermally decomposed to form $NO_2$ and transferred to a reaction cell containing an aqueous, alkaline, luminol-containing solution. The $NO_2$ reacts with the luminol to produce light by chemiluminescence. A light detector registers the presence of this light as indicative of the detection of the contraband substance, and activates a signaling device to provide an audible or visible alarm. The apparatus rapidly detects the presence of a wide variety of contraband substances in an accurate, reliable manner. It provides for automated screening, with the result that vagaries of human performance are virtually eliminated. False alarms are reduced and detection efficacy is increased. A traceable residue of the detected contraband is left on the article for use in forensic analysis. This system does not use a MOS detector to detect explosives.

The 2007 Ph.D. Thesis by Maria Monterola submitted to University of Florida discloses laser photofragmentation and heterogeneous chemiluminescence for nitrogen-based explosive detection. The decomposed explosives forming $NO_2$ are reacted with luminol to create chemiluminescence, which is measured. No MOS detector is used to detect the presence of explosive.

The 2013 Ph.D. Thesis by Yun Chu submitted to University of Rhode Island discloses solid state gas sensors for detection of explosives and explosive precursors. A thermodynamic based thin film gas sensor which can reliably detect various explosive compounds was developed and demonstrated. The principle of the sensors is based on measuring the heat effect associated with the catalytic decomposition of explosive compounds present in the vapor phase. The decomposition mechanism is complicated and not well known, but it can be affected by many parameters including catalyst, reaction temperature and humidity. Explosives that have relatively high vapor pressure and readily sublime at room temperature, like TATP and 2, 6-DNT, are ideal candidates for vapor phase detection using the thermodynamic gas sensor. ZnO, W2O3, V2O5 and SnO2 were employed as catalysts. This sensor exhibited promising sensitivity results for TATP, but poor selectivity among peroxide based compounds. The heat generated at the sensor is used to determine the presence of the explosive, through the resistance change of thin inorganic film.

The 2014 Ph.D. Thesis by Danling Wang submitted to University of Washington discloses trace explosive sensor devices based on semiconductor nanomaterials. This dissertation discusses an explosive sensing device based on semiconductor nanomaterials. Two kinds of materials: titanium dioxide nanowires and silicon nanowires are used to detect explosive trace vapor. It was found that the high porous $TiO_2(B)$ nanowires when mixed anatase $TiO_2$, exhibit a very fast and highly sensitive response to nitro-containing explosive molecules to detect explosives. It shows the specific surface characteristics of $TiO_2$ responsible for the nitrocontaining explosives. The MOS detection devices do not use tin oxide, indium tin oxide sensing elements.

The publication by Prabakaran Shanka et al. ScienceJet 2015, vol. 4: page 126 discloses "Gas sensing mechanism of metal oxides: The role of ambient atmosphere, type of semiconductor and gases—A review". Nitrogen dioxide is a strong oxidizing agent and has strong electrophilic properties, which enable this molecule to be quickly adsorbed on the metal oxide surface. $NO_2$ can react with metal oxide surface both in the presence and absence of oxygen. It can be seen that the oxidation of $NO_2$ leads to the reduction of conduction electrons in the conduction band. Reducing gases are those which act as electron donors when interacting with metal oxide surface. During this interaction, reducing gases desorb or remove the chemisorbed oxygen ions and physisorbed hydroxyl ions from the metal oxide surface. The variation in the resistance of the material is used to detect the concentration of reducing gases such as $SO_2$, CO, $H_2$, $NH_3$, $H_2S$ and $C_2H_5OH$ by the chemical changes following REDOX reaction.

Notwithstanding the aforementioned schemes both for sample collection and analysis, there remains a need in the art for integrated systems capable of reliably, accurately, and rapidly detecting the presence of explosives. More particularly, there is need for systems that are readily automated for semi-continuous or continuous inspection and detection of the presence of residues of such materials on luggage, cargo, vehicles, freight containers, and related items. Such systems are highly sought, especially in the context of airport screening, but would be equally valuable for courthouses, stadiums, schools, government offices, military installations, correctional institutions, and other public venues that might be targets of terrorist or similar criminal activity.

SUMMARY OF THE INVENTION

The present invention provides a method and system for detecting small quantities of explosives located on the surfaces of objects. The surface of an object is wiped to collect the surface contamination present and is loaded to the desorber wherein it is subject to pyrolysis, and vapor products produced are pumped to the measurement apparatus of the detection system. The detection system component comprises two separate sensor based measurements one of which uses chemi-luminescence from a 5-amino-2,3-dihydro-1,4-phthalazine dione (luminol) solution determining the approximate quantity of the explosive or other gaseous products generated. An alkaline solution of luminol, pH in the range of 8 to 14, releases photons through chemiluminescence and is measured using a photo multiplier tube detector. The second system is a set of highly sensitive MOS detectors determining the presence of nitrogen containing or nitrogen free explosive. Since the MOS devices are sensitive to the presence of nano grams of explosives, it is important that the amount of pyrolysis generated vapor quantity passed into the detection system be controlled so as to not saturate the measurement capability of the very sensitive MOS sensors.

The luminol based first sensor provides guidance for the amount of pyrolysis generated vapors into the MOS detection system. The technique employs a chemical reaction between luminol and $NO_2$ gas from pyrolysis of nitrogen containing explosives as well as the pyrolysis of explosives without nitrogen resulting in carbon monoxide and carbon dioxide. Luminol is typically in an aqueous, alkaline solution with a pH in the range of 8 to 14. Under suitable conditions, the vast majority of common explosive types may be decomposed to produce $NO_2$ gas that is detected using the apparatus presented herein. The luminol reaction is known to produce light by a process termed chemiluminescence. This light, in turn, is detected to signal the presence of the explosive substance. The intensity of light produced indicates the amount of explosives present in the pyrolysis measurement sample and is used as guidance for the detection of explosives by the second MOS array sensor, which is very sensitive and is subject to saturation.

The second sensor is an array of MOS sensors with a ceramic or fused silica substrate having a metallic heating element provided on the underside of the substrate. The upper surface of the substrate is coated with an oxide composition, typically tin oxide, indium tin oxide, tungsten oxide. These oxides are semi-conductors and the resistivity of the deposited layer is decreased or increased when $NO_2$ or $CO_2$ is adsorbed from the gas phase at the external surface of the deposited oxide layer.

In an alternate embodiment, the quantity of pyrolysis gases of an explosive are passed to an array of very sensitive MOS sensors to detect the presence of explosive. The metering of the pyrolysis generate gases is carried out by a metering valve preventing saturation of the very sensitive MOS sensors.

Generally stated, the method comprises the steps of: (i) producing $NO_2$ or $CO/CO_2$ by decomposition of nitrogen containing or nitrogen free explosive substance; (ii) transferring the $NO_2$ or $CO_2$ to a reaction which contains an aqueous, alkaline luminol solution; (iii) reacting, within a reaction cell, the $NO_2$ or $CO_2$ with luminol in the presence of $O_2$ to produce light by chemiluminescence; and (iii) detecting the light with a light detector to indicate the presence of the explosive substance. This detection measurement indicates the amount of explosive present. (ii) Transferring a smaller portion of the reaction product of $NO_2$ or $CO_2$ to a very sensitive MOS sensor to detect the presence of to a very sensitive MOS detector. The system of the invention can detect the presence of nitrogen containing or nitrogen free explosive substances.

Also provided by the invention is a system for screening for the presence of explosives, the system comprising: (a) collection means for collecting explosive residues; (b) loading means for loading said collected residues into a desorber; (c) pyrolysis means for pyrolysing said explosive residue to generate a gaseous sample; (d) first pumping means for pumping the gaseous sample sequentially into a luminol reaction cell followed by a very sensitive metal oxide sensor (MOS) array; (e) said luminol producing chemiluminescence by a chemical reaction between said luminol and said gaseous sample within said reaction cell; (f) photomultiplier tube measuring means, for measuring the intensity of chemiluminescence and for outputting a first electrical signal indicative of the amount of explosive detected; (g) second pumping means for pumping a reduced quantity of said gaseous sample to said metal oxide sensor array, to prevent saturation of metal oxide detector; (h) resistance measuring means, for measuring resistance of oxide film on the metal oxide sensor, said resistance being changed by adsorption of said pumped gaseous sample; (i) said resistance measurement indicating the presence of said explosive; whereby the chemiluminescence measurement is refined by the metal oxide sensor measurement to eliminate the interference composition from detection.

In yet another aspect the invention provides a system for screening for the presence of explosives, the system comprising: collection means for collecting explosive residues; loading means for loading said collected residues into a desorber; pyrolysis means for pyrolysing said explosive residue to generate a gaseous sample; pumping means for pumping the gaseous sample to a very sensitive metal oxide sensor (MOS) array; metering means for reducing the quantity of said gaseous sample to said metal oxide sensor array, to prevent saturation of metal oxide detector; resistance measuring means, for measuring resistance of oxide film on the metal oxide sensor, said resistance being changed by adsorption of said pumped gaseous sample; said resistance measurement indicating the presence of said explosive.

The disclosed method comprises a pyrolysis step that produces $NO_2$ or $CO/CO_2$, by pyrolyzing particles collected. Sufficient $NO_2$ or $CO/CO_2$i produced is detectable using the luminol reaction, thereby rendering the presence of the contraband substance detectable, even if the amount thereof is quite limited. The specific minimum amount of explosive or other contraband that is detectable depends on the material, but may be as low as the sub-nanogram level.

The present system is adapted for the detection of a wide variety of explosive substances for which detection is desired. The chemical analysis systems disclosed herein can be readily adjusted and suitably calibrated and operated to be sensitive and selective for detection of such materials, notably including modern explosive materials such as C4, SEMTEX, and DM12.

BRIEF DESCRIPTION OF THE DRAWINGS

The invention will be more fully understood and further advantages will become apparent when reference is had to the following detailed description of the preferred embodiments of the invention and the accompanying drawings, wherein like reference numerals denote similar elements throughout the several views, and in which.

DESCRIPTION OF THE PREFERRED EMBODIMENTS

Figure 1:
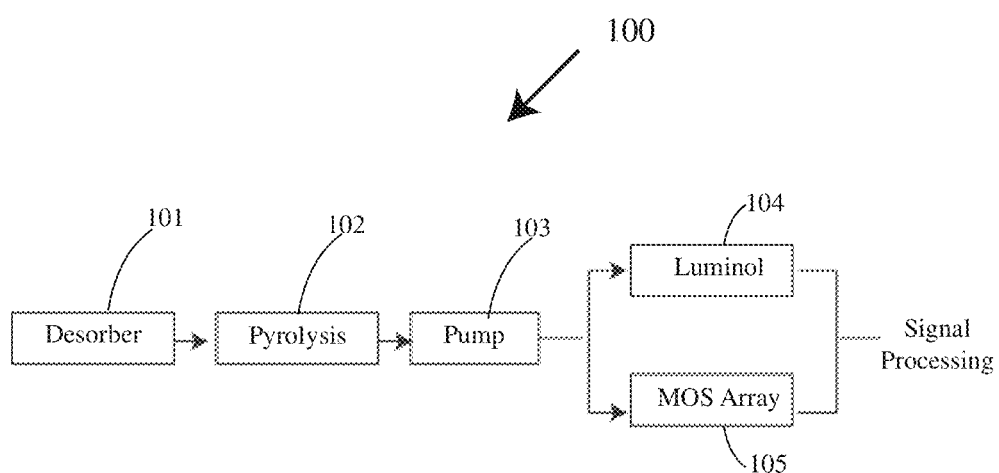
FIG. 1 is a schematic view of an explosive detection system of the invention using two parallel systems one using a luminol detector and the other using a MOS detector.

The present invention provides an apparatus and method for analyzing surface explosive residue suspected of containing one or more explosive agents using the chemiluminescent, gas-liquid phase reaction of luminol and MOS sensors detecting $NO_2$ and $CO/CO_2$.

A number of explosive compositions are known. Trinitrotoluene (TNT) has the following structure. TNT is nitrated from toluene in three steps, employing nitric acid and sulphuric acid mixtures as nitrating agent. TNT has a negative OB, meaning it contains insufficient oxygen to give complete combustion of the carbon on detonation. It is therefore, usefully is mixed with ammonium nitrate, which has an excess of oxygen.

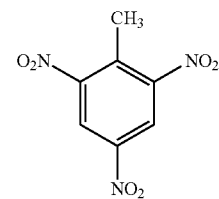 [SMILES: Cc1c([N+](=O)[O-])cc([N+](=O)[O-])cc1[N+](=O)[O-]]

Another explosive pentaerythritol tetranitrate (PETN) has the following molecular structure. Pentaerythritol is made commercially by the reaction of formaldehyde and acetaldehyde in the presence of alkali. It is then nitrated by adding it to strong nitric acid at temperatures below about 30° C. PETN is very stable both chemically and thermally, but is sensitive to shock and friction. Upon ignition, the oxygen atoms in the nitrate sub-group terminals oxidize the carbon and hydrogen atoms in the interior of the molecule.

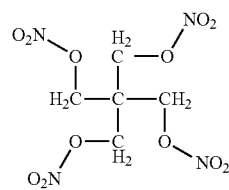

Another explosive cyclotrimethylenetrinitramine (RDX) has the following molecular structure. It is a white crystalline powder made by the nitration of hexamine (hexamethylenetetramine) with nitric acid and ammonium nitrate below 30° C. RDX is widely used as in both military and industries as a base component of explosives compounds, such as plastic explosives, and is considered one of the most stable and powerful high explosives.

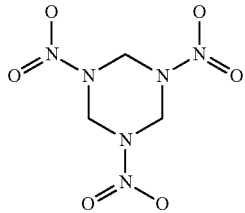

Another nitrogen containing explosive is Hexamethylene triperoxide diamine (HMTD). HMTD is another common homemade primary explosives used by terrorists in suicide bombings and other attacks. It is made from hydrogen peroxide ($H_2O_2$) and Hexamethylenetetramine (($CH_2)_6N_4$) in presence of citric acid or dilute sulfuric acid as catalyst. HMTD is extremely sensitive to shock, heat and friction, making it dangerous to manufacture but ideal as a detonator. HMTD has been used in a large number of suicide bombing and other terrorist attacks all over the world.

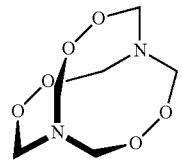

Another nitrogen free explosive is triacetone triperoxide (TATP). TATP is an organic peroxide explosive which is extremely sensitive to heat, shock and friction. It is produced from hydrogen peroxide ($H_2O_2$) and acetone ($C_3H_6O$) in presence of strong acid (sulfuric acid). In mildly acid or neutral condition, the reaction will produce more diacetone diperoxide (DADP) or even acetone peroxide monomer than TATP. TATP has a relatively high vapor pressure, which allows it sublime under room temperature. Also, it is a very powerful explosive which produces approximately 80% of outward force that TNT produces with the same amount of explosive. Due to its readily available material and easy to synthesize, TATP has been used as the initiator in many terrorist attacks.

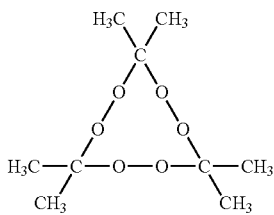

Virtually all common explosive types, including organo-nitro explosives, as well as nitrogen free explosives may be decomposed under suitable conditions to produce $NO_2$ and $CO/CO_2$. In one aspect of the invention, the decomposition comprises pyrolysis of nitrogen containing explosives according to reactions of the following type:

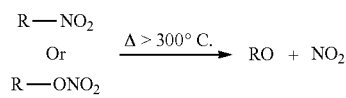

Nitrogen free explosive such as TATP undergoes similar reaction releasing CO and $CO_2$. The pyrolysis reaction ordinarily requires a suitable heating means for efficient production of $NO_2$ or CO and $CO_2$. It has been found that heated Nichrome or Pt, while a heated Pt—Rh alloy is preferred. The heating temperature for pyrolysis is typically in the range of about 300 to 800° C., and more preferably, the temperature ranges from about 500 to 700° C.

The first detector uses luminol chemiluminescence to detect the presence of explosive in the sample being subject to pyrolysis. Luminol (5-amino-2,3-dihydro-1,4-pthalazine dione) is known to react with $NO_2$ in the presence of oxygen to produce light at a wavelength centered at about 425 nm according to the following reaction:

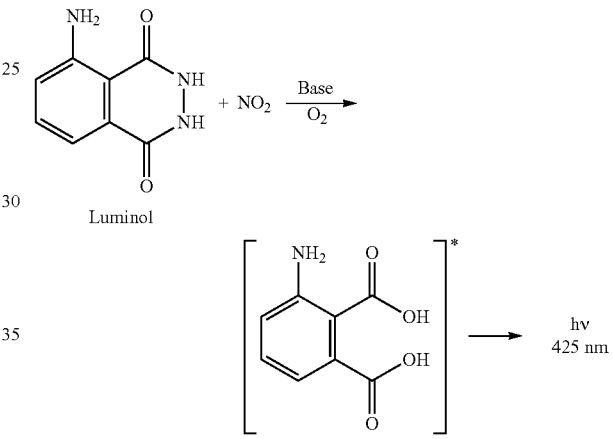

The selectivity of the present system for $NO_2$ is enhanced by providing luminol in an aqueous, alkaline solution. Use of potassium hydroxide (KOH) as the base is preferred, as it surprisingly has been found to increase the chemiluminescent light output over that resulting from solutions comprising other bases such as sodium hydroxide (NaOH). The light thereby produced can readily be detected by a light detector, such as a photomultiplier tube (PMT). Advantageously, conventional PMT's are quite sensitive to light of this wavelength.

Referring now to FIG. 1 of the drawings, there is depicted at 100 a schematic view of an explosive detection system of the invention using two parallel systems one using a luminol detector 104 and other detector 105 using a MOS detector. The explosive residue is collected by wiping or vacuum suction means and is desorbed in a carrier at 101, which is then subject to pyrolysis at 102 releasing $NO_2$ or $CO/CO_2$. It is then pumped at 103 sequentially to separate station one containing a luminol solution and a second detector containing MOS sensors. Since the MOS detectors are very sensitive, the inlet of the pumped $NO_2$ or $CO/CO_2$ gases is reduced to prevent saturation of the MOS detectors.

Figure 2:
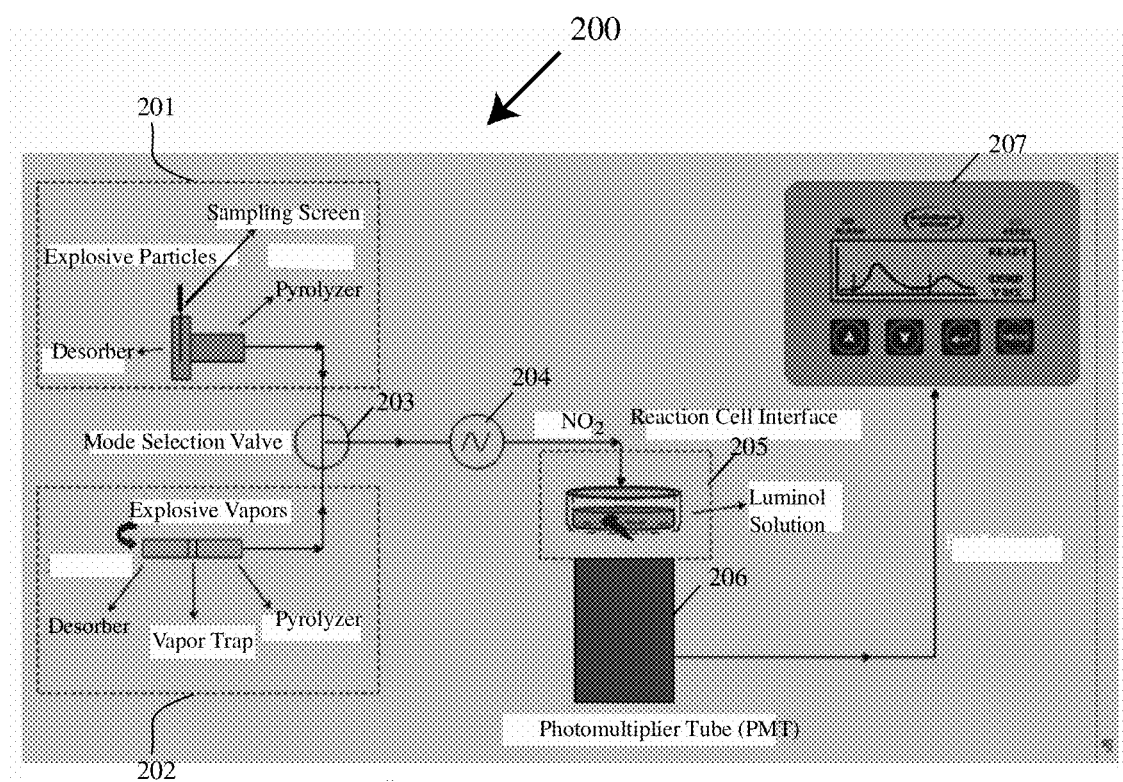
FIG. 2 is a perspective view of the luminol explosive detection system of the invention.

FIG. 2 is a perspective view of the luminol explosive detection system of the invention at 200. The detection technology relies on thermal decomposition of explosives such as RDX, PETN, AN, UN, TNT, NG, TATP, Chlorate, perchlorate, $H_2O_2$ and Taggants yielding to the formation of chemicals which specifically react with luminol to generate light. The explosive powder detection portion is shown at 201, Explosive vapor detection is shown at 202. The mode selection valve 203 selects which pyrolyzed explosive is sent to the pump 204. The luminol reaction cell is shown at 205. The luminol solution is packaged into a scintillation vial equipped with a semi-permeable membrane, which allows $NO_2$ to react with the luminol and at the same time prevent any possible leakage from the cell. The operator easily replaces the cartridge after several weeks of operation. The amount of light generated by this chemiluminescence reaction is directly proportional to the amount of explosives analyzed and is detected by photomultiplier tube 206. The chemiluminescence data is sent to display 207.

Figure 3:
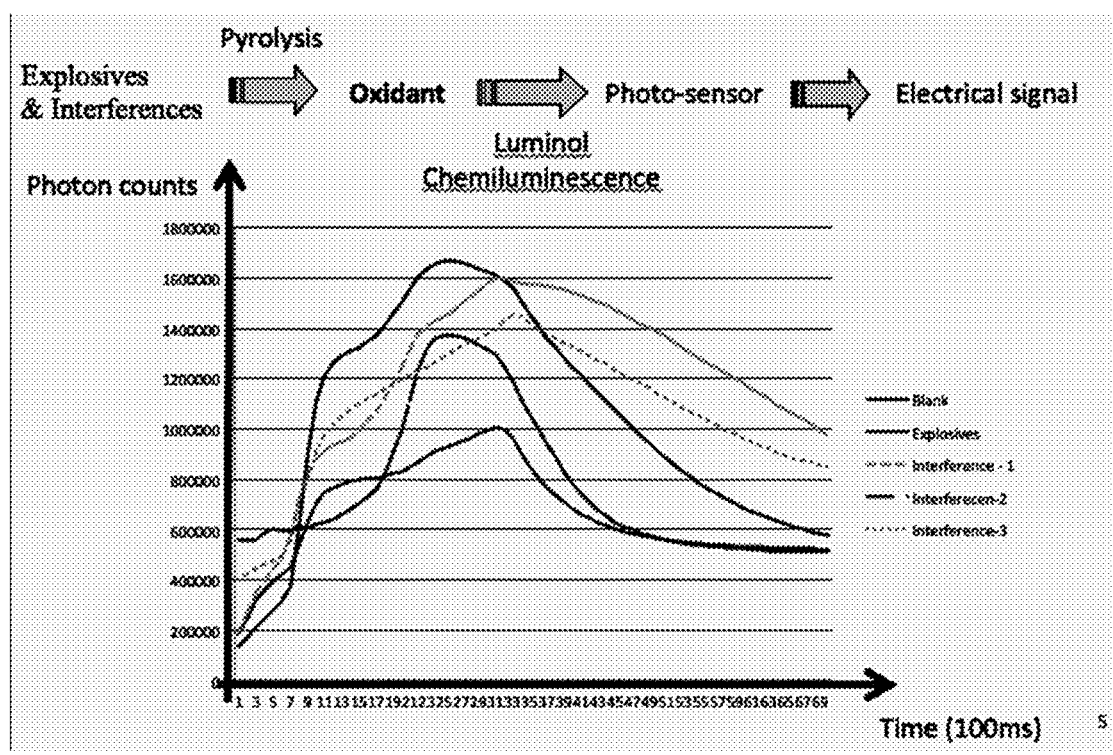
FIG. 3 is a schematic representation of chemiluminescence of luminol under different conditions.

FIG. 3 is a schematic representation of chemiluminescence of luminol under different conditions. Clearly explosives show a very large chemiluminescence response. A number of interference species also produce significant chemiluminescence. The explosive response is maximum at about 29 seconds with a broad peak extending to several seconds as luminol is consumed by the chemical reaction of luminol with $NO_2$ and $CO/CO_2$.

Figure 4A:
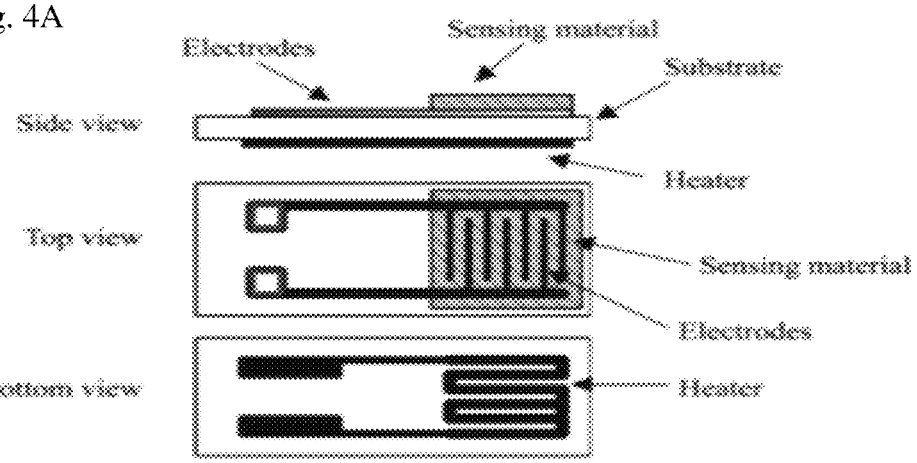
FIG. 4A is a schematic representation of the constructional details of the MOS sensor.

FIG. 4A is a schematic representation of the constructional details of the MOS sensor. A conductivity sensor is a sensing system that measures the change in conductivity due to the interaction between sensing material and explosive molecules. The substrate is a thin ceramic or fused silica sheet with heater on nickel or nickel chromium or platinum heating elements to heat the substrate to about 700° C. The top surface of the sensor has oxide layer sensing material and electrodes are provided to measure the conductivity.

Figure 4B:
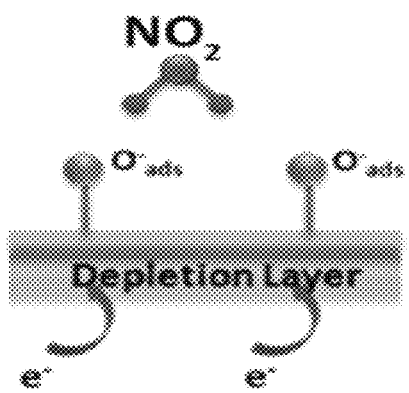
FIGS. 4B and 4C illustrate the detection mechanism detection capability of $NO_2$ and $CO/CO_2$.
Figure 4C:
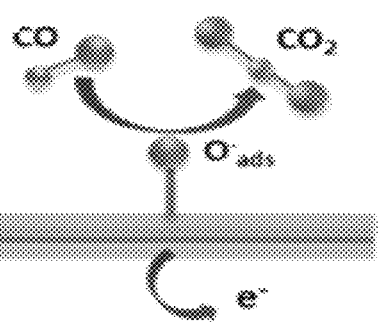

FIGS. 4B and 4C illustrate the detection mechanism detection capability of $NO_2$ and $CO/CO_2$. $NO_2$ oxidizes the surface of the oxide sensing layer increasing electrical resistance at the grain boundaries. $CO/CO_2$ reduces the surface of the oxide sensing layer decreasing electrical resistance at the grain boundaries.

The operation of the metal oxide conductivity sensor is illustrated at FIGS. 4B and FIG. 4C. When $NO_2$ gas from pyrolysis reacts with the metal oxide surface as shown at FIG. 4B, it oxidizes the surface layer to form a depletion layer that creates negatively charged electrons. The grain boundaries of the polycrystalline metal oxide are strengthened by the oxidation and the overall resistance of the film increases. Accordingly, the resistance of the oxide layer increases and the measurement system registers this as a reduction in voltage. When $NO_2/CO/CO_2$ gas from pyrolysis reacts with the metal oxide surface as shown at FIG. 4C, it reduces the surface layer, creating negatively charged electrons. The grain boundaries of the polycrystalline metal oxide are weakened by the reducing action and the overall resistance of the film decreases. Accordingly, the resistance of the oxide layer decreases and the measurement system registers this as an increase in voltage.

Conducting metal oxides are mostly semiconductors, which are the most commonly utilized classes of sensing materials in conductivity sensors, and this figure demonstrates typical schematics of a conductometric sensor. Metal oxide gas sensors based on measuring the conductivity change of the semiconducting materials, or known as conductometric sensors, are one of the most investigated groups of gas sensors due to their low cost and flexibility associated to their production, simplicity of their use and wide possible application fields. The cause of change of sensor conductivity can be traced down to two major causes: physical process and chemical process. One is that when the chemicals are physically adsorbed to the surface of metal oxide, transfer of charge carriers (electrons or holes) between semiconductor and adsorbed species or their catalytic decomposition products leads to the conductivity changes. The other reason is that the chemicals or their catalytic decomposition products is very reactive, either oxidizing or reducing the metal oxide to a different oxidation state which will then alter the electrical property of the semiconducting material.

Figure 5:
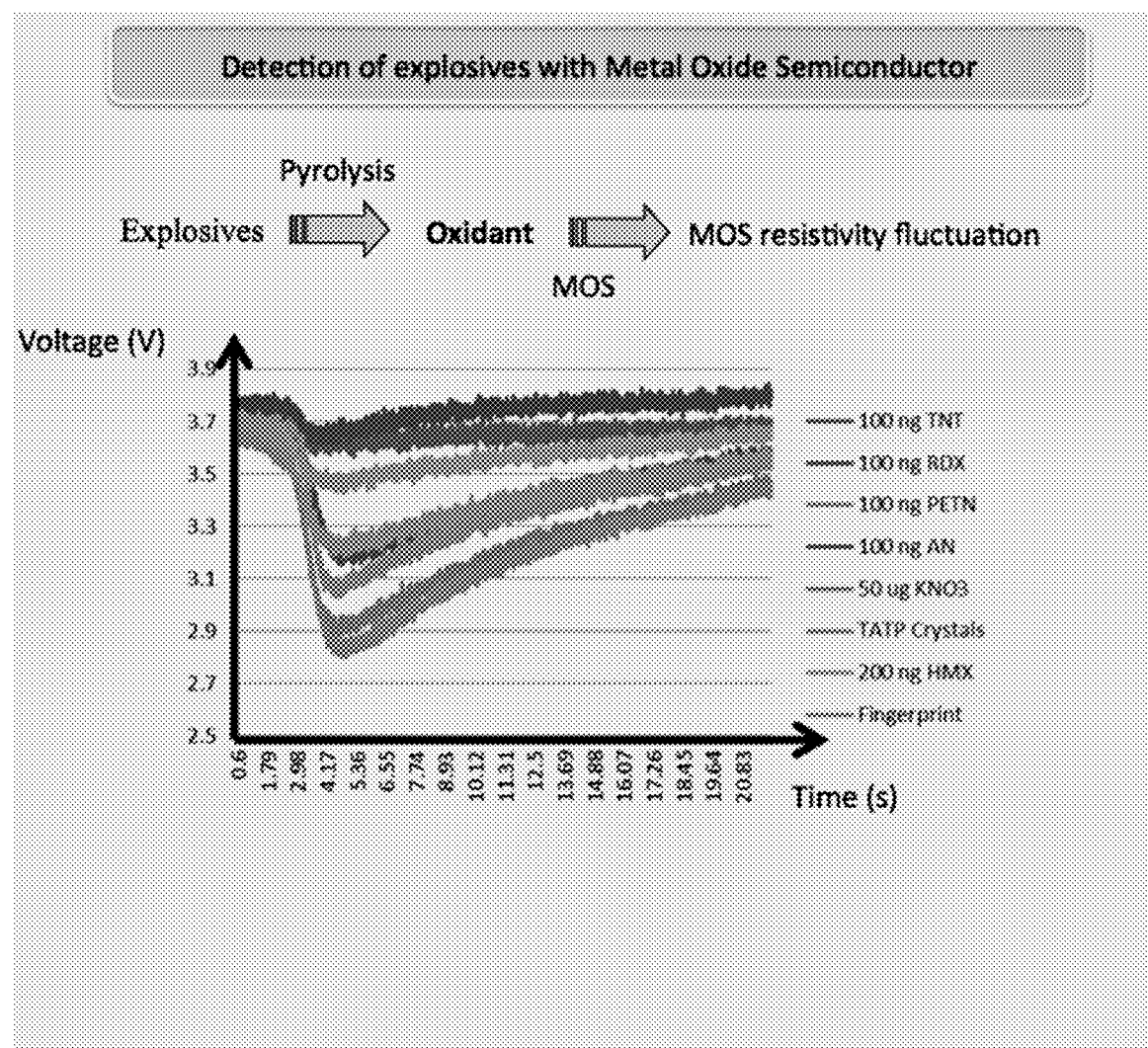
FIG. 5 is a graph showing resistivity change of the MOS detector for various explosive compounds.

FIG. 5 shows graphs the resistivity change of the MOS detector for various explosive compounds. All the explosives except TATP are nitrogen containing explosives. All the explosives show a strong reduction in measured voltage across conductors on the oxide film, the minimum occurring at about 5 seconds. When absorption of the $NO_2$ is small, the sensor resistance recovers within a short time (typically about 12 seconds), while some explosives do not recover well for a prolonged time period.

Figure 6:
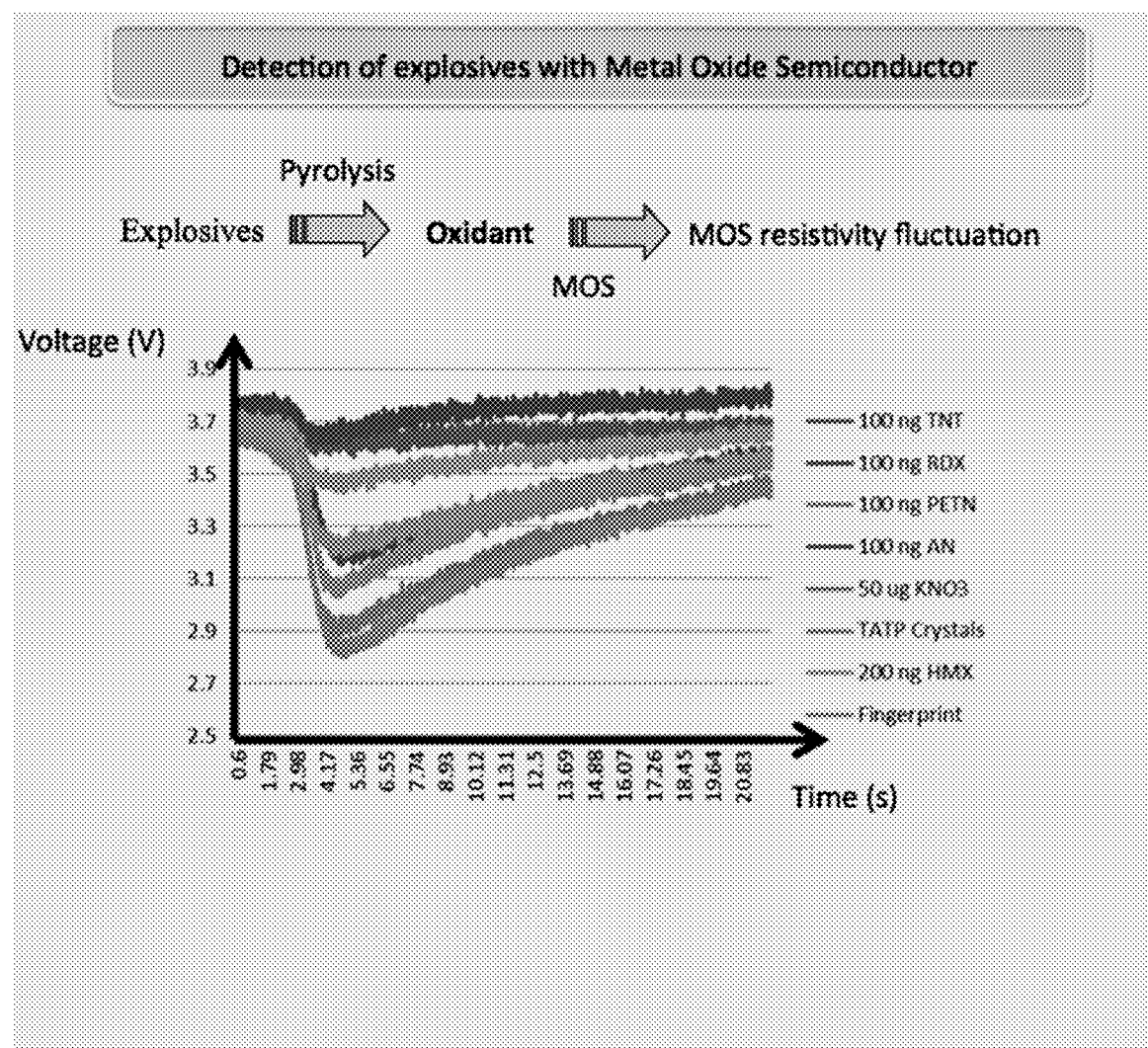
FIG. 6 is a graph depicting the signal intensity of the MOS sensor and recovery time as a function of amount of PETN in the pyrolysis tube.

FIG. 6 is a graph depicting the signal intensity of the MOS sensor and recovery time as a function of the amount of PETN in the pyrolysis tube. The minimum still occurs at about 5 seconds. When the absorption of the $NO_2$ is small, the sensor resistance recovers within a short time (about 12 seconds). When explosives quantity is high, for example 100 ng of PETN, the resistance of the oxide film is not readily recovered even after 20 seconds.

Figure 7:
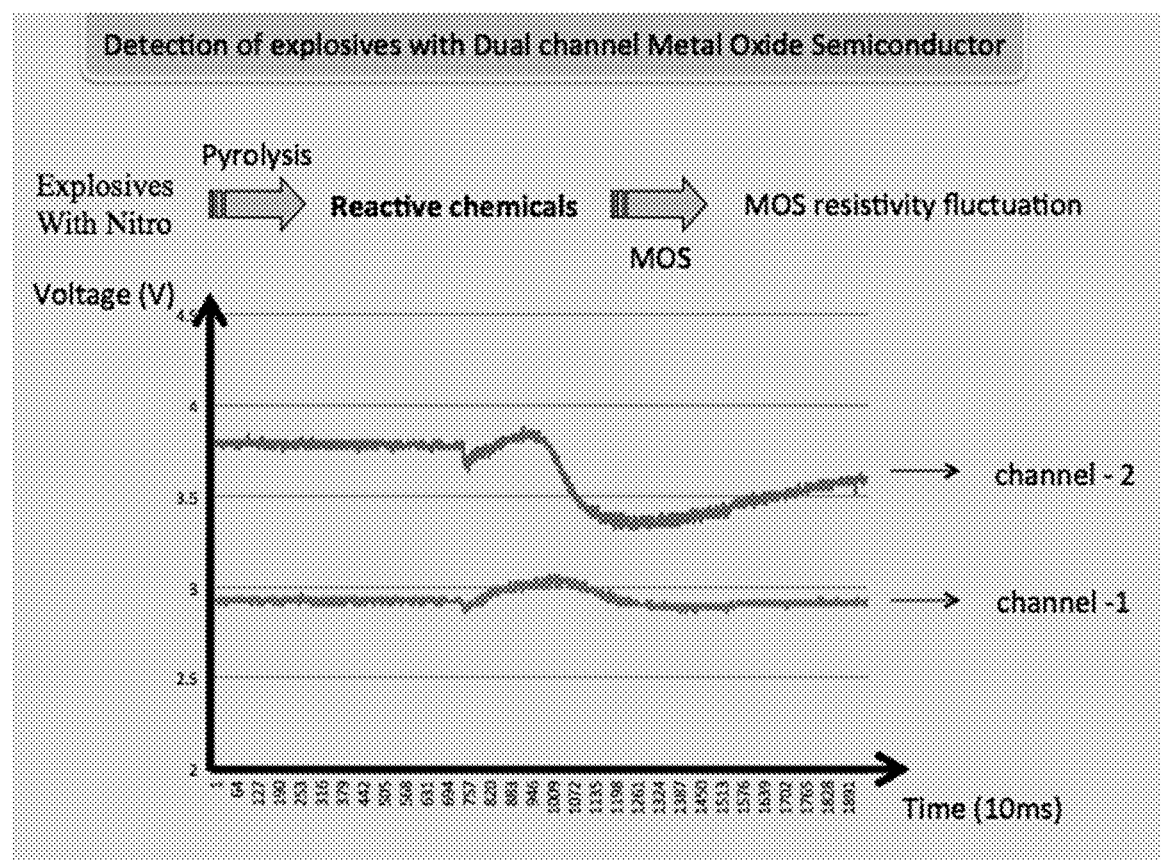
FIG. 7 is a graph depicting the detection of explosives of nitrogen containing explosive with dual channel metal oxide semiconductor.

FIG. 7 is a graph depicting the detection of nitrogen containing explosive with a dual channel metal oxide semiconductor. Channel 1 detects $CO/CO_2$ while channel 2 detects $NO_2$. When channel 1 detects $CO/CO_2$, the voltage goes up indicating that the resistance of the oxide film has decreased by the reducing action of $CO/CO_2$. Since this is a nitrogen containing explosive, channel 1 response is minimal. When channel 2 detects $NO_2$, the voltage decreases, indicating that the resistance of the oxide film has increased by the oxidizing action of $NO_2$.

Figure 8:
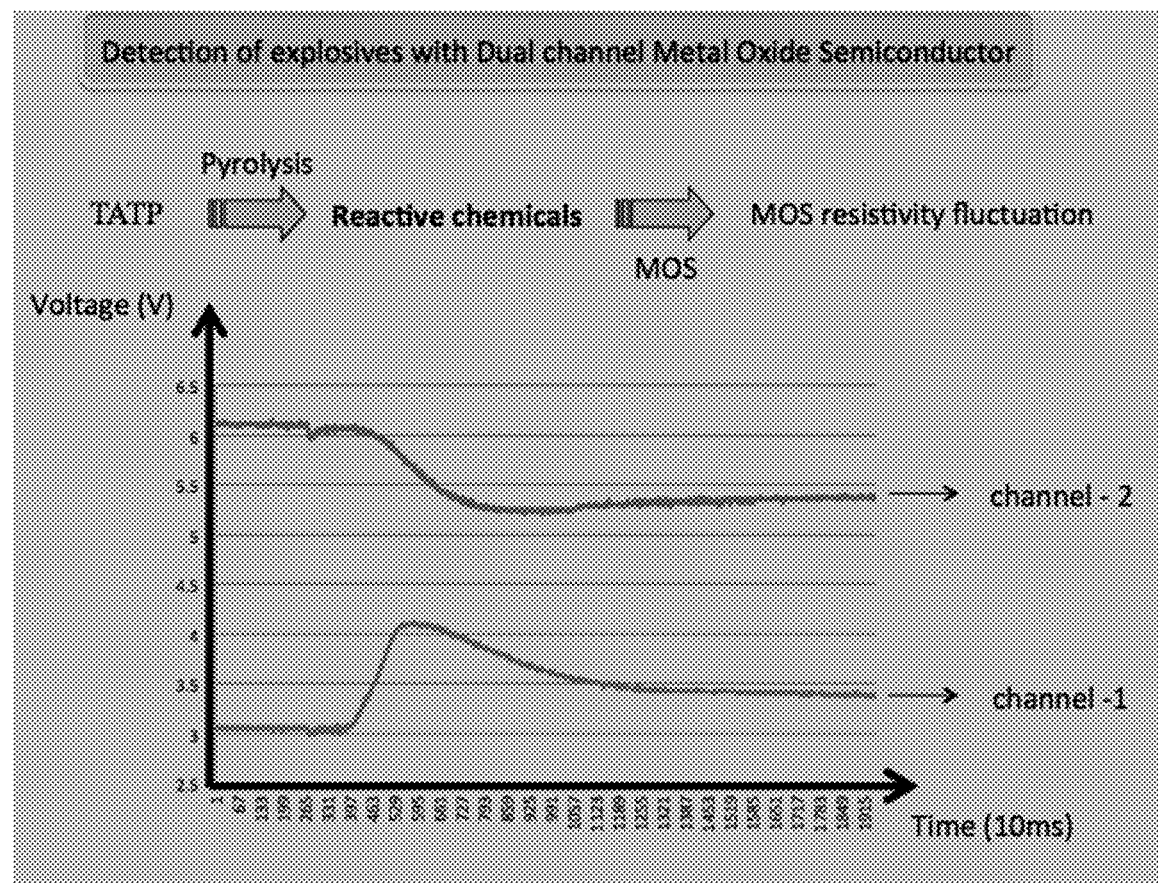
FIG. 8 is a graph depicting the detection of explosives of nitrogen free explosive TATP with dual channel metal oxide semiconductor.

FIG. 8 is a graph depicting the detection of explosives of nitrogen free explosive TATP with a dual channel metal oxide semiconductor. TATP is a non nitrogen containing explosive. Channel 1 detects $CO/CO_2$ while channel 2 detects $NO_2$. When channel 1 detects $CO/CO_2$, the voltage goes up indicating that the resistance of the oxide film has decreased by the reducing action of $CO/CO_2$. Since this is a non nitrogen containing explosive, channel 2 response is minimal. When channel 1 detects $CO/CO_2$, the voltage increases, indicating that the resistance of the oxide film has decreased by the reducing action of $CO/CO_2$.

Figure 9:
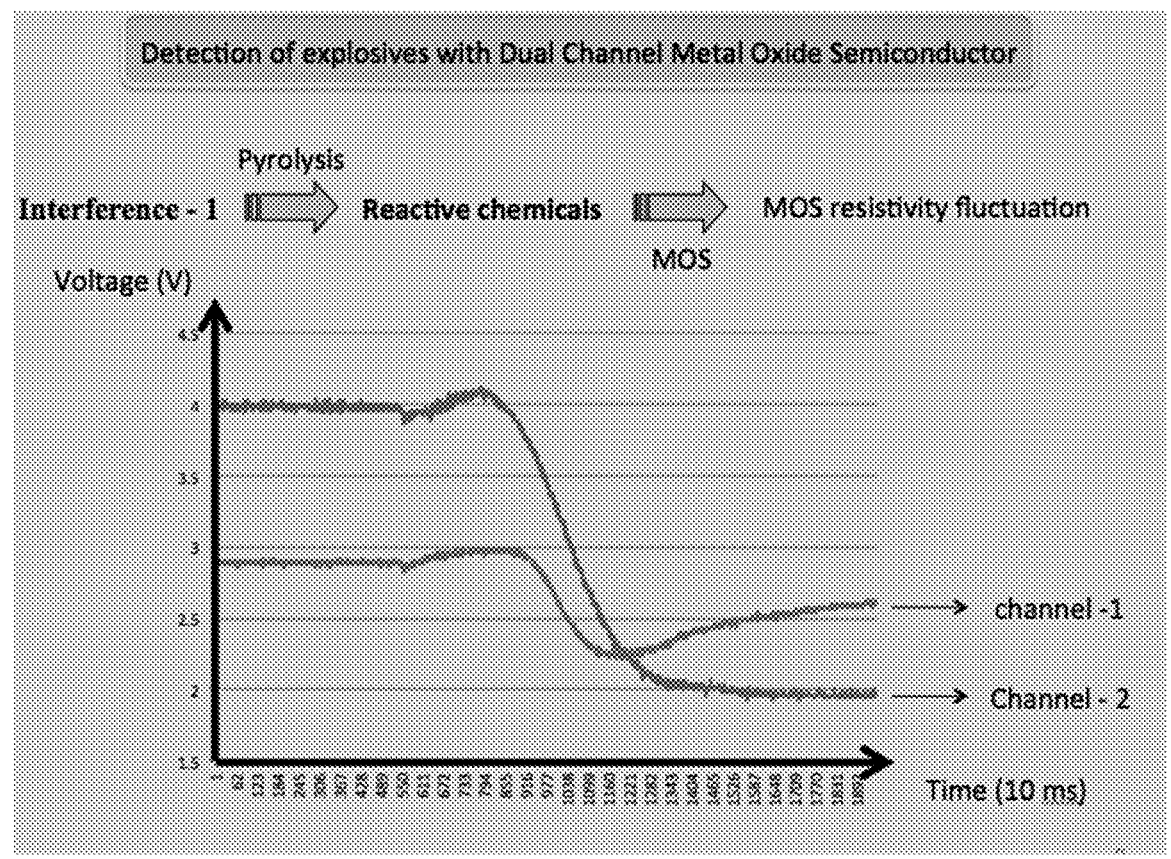
FIG. 9 is a graph depicting the detection of explosives of interference 1 composition with dual channel metal oxide semiconductor.

FIG. 9 is a graph depicting the detection of explosives of interference 1 composition with dual channel metal oxide semiconductor. The interference 1 composition is leather. Leather contains both carbon and nitrogen and the pyrolysis products contain both $NO_2$ and $CO/CO_2$. Accordingly, both channel 1 and channel 2 show a strong response, indicating that interference 2 composition is not an explosive.

Figure 10:
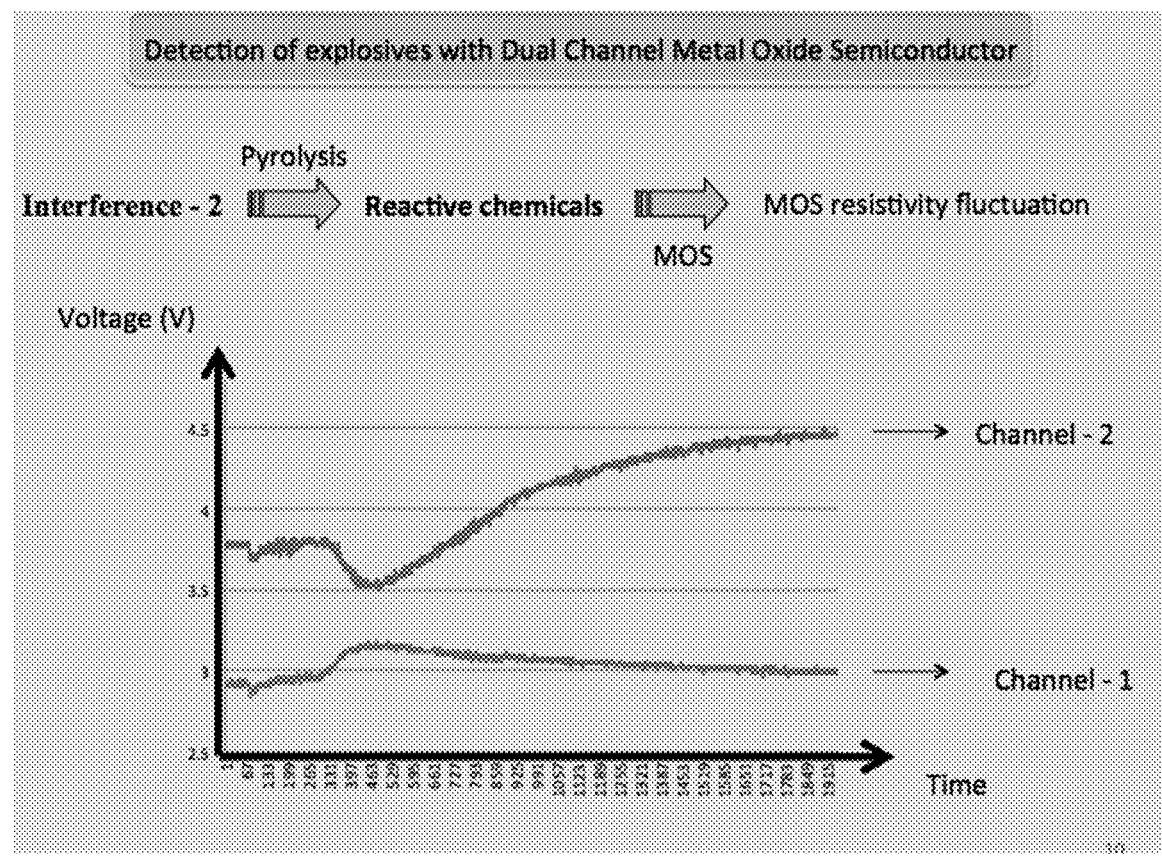
FIG. 10 is a graph depicting the detection of explosives of interference 2 composition with dual channel metal oxide semiconductor.

FIG. 10 is a graph depicting the detection of explosives of interference 2 composition with dual channel metal oxide semiconductor. The interference 2 composition is a protective glove. The protective glove contains both carbon and nitrogen and the pyrolysis products contain both $NO_2$ and $CO/CO_2$. Accordingly, both channel 1 and channel 2 show a strong response indicating that interference 2 composition is not an explosive.

Figure 11:
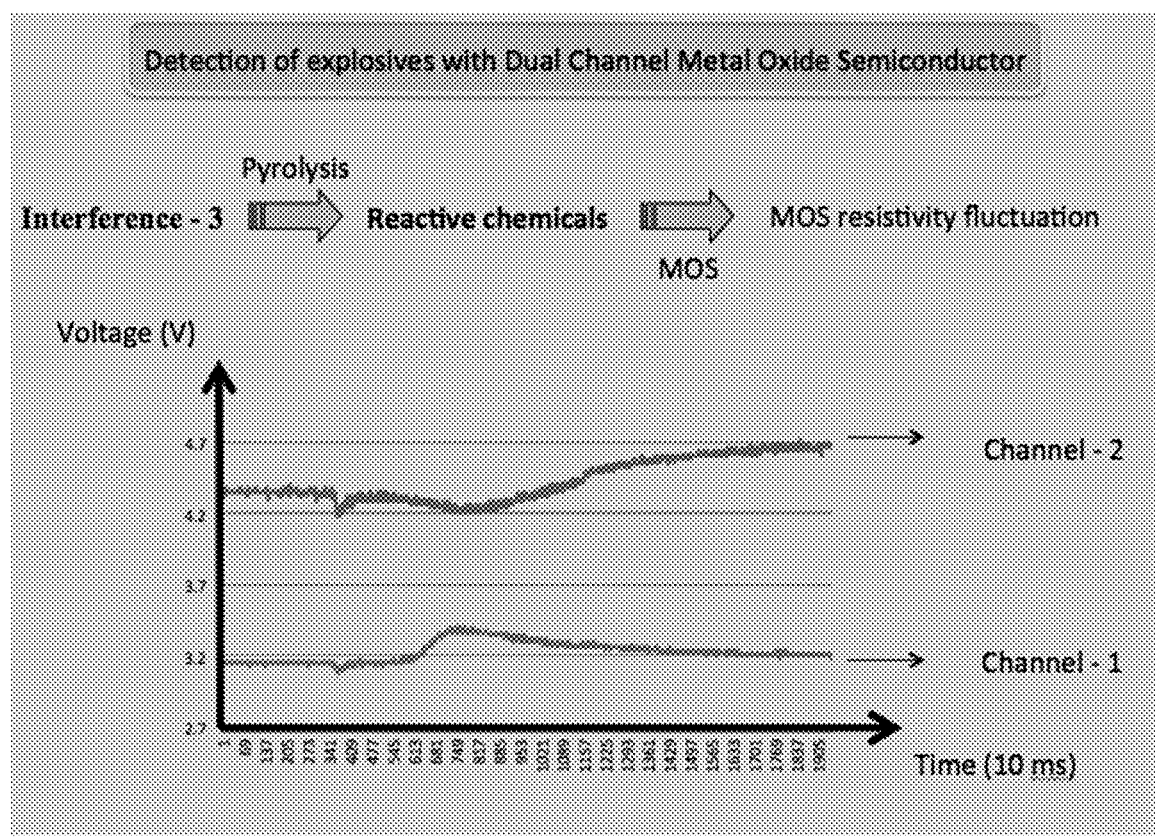
FIG. 11 is a graph depicting the detection of explosives of interference 3 composition with dual channel metal oxide semiconductor.

FIG. 11 is a graph depicting the detection of explosives of interference 3 composition with dual channel metal oxide semiconductor. The interference 2 composition is a finger pint residue. The finger print residue contains both carbon and nitrogen and the pyrolysis products contain both $NO_2$ and $CO/CO_2$. Accordingly, both channel 1 and channel 2 show a strong response indicating that interference 3 composition is not an explosive.

Figure 12:
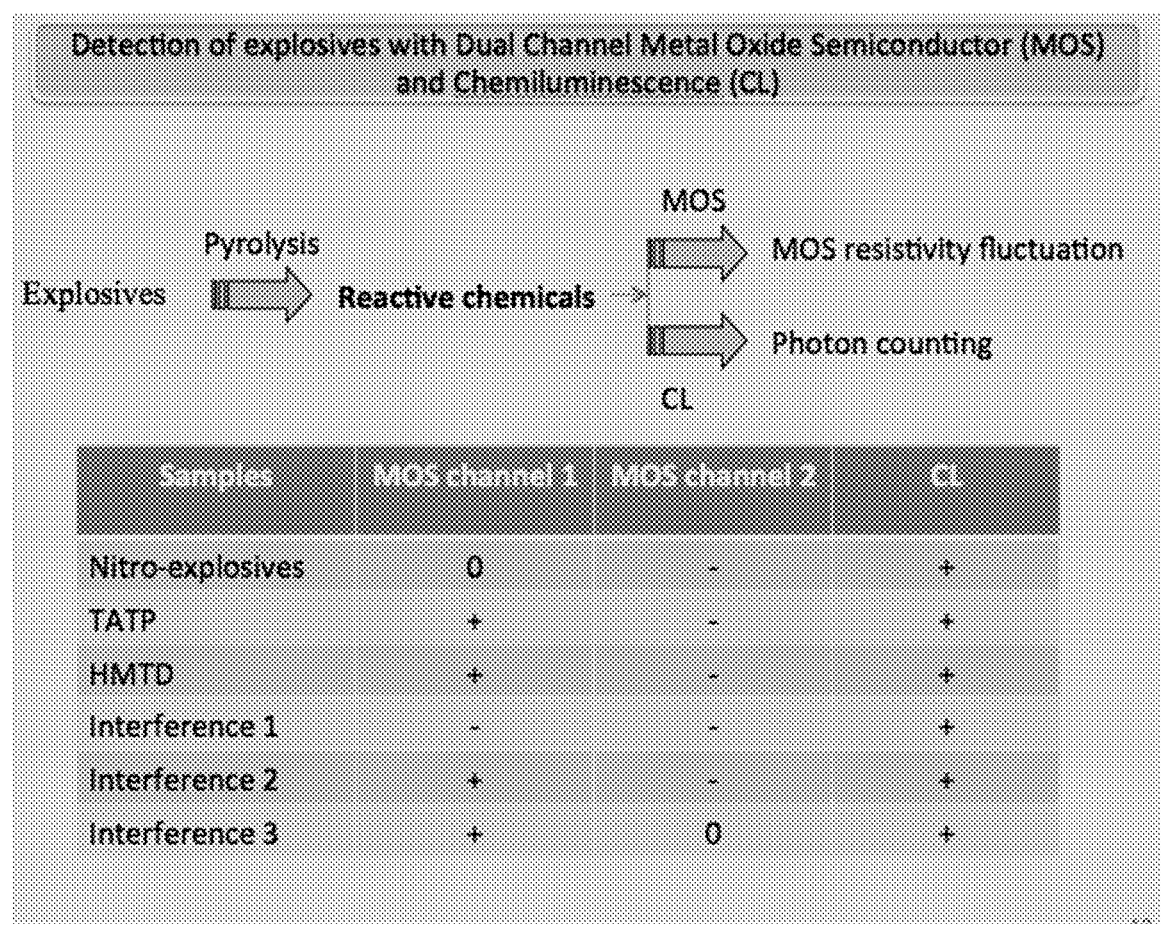
FIG. 12 shows comparison of MOS detector response for $NO_2$ (channel 2) and $CO/CO_2$ (channel 1) for nitrogen containing explosive, nitrogen free explosive and interference compositions 1, 2 ND 3.

FIG. 12 is a table that shows a comparison of MOS detector response for $NO_2$ (channel 2) and $CO/CO_2$ (channel 1) for nitrogen containing explosive, nitrogen free explosive and interference compositions 1, 2 and 3. In this table '+' means that a positive response is observed from the initial peak, '−' means that a negative response is observed from the initial peak, '0' means that nearly a flat response is observed from the initial peak. Also shown in the last column is the chemiluminescent response. Thus the MOS sensors identify the explosives even when chemiluminescent response is absent.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A system for screening for the presence of nitrogen containing explosives, the system comprising:
    a. a chamber for collecting explosive residues;
    b. a desorber;
    c. a pyrolysis tube for pyrolyzing said explosive residue to generate a gaseous sample from decomposition of the explosive residues comprising $NO_2$;
    d. a pump for pumping the gaseous sample sequentially into a luminol reaction cell followed by transferring a smaller portion of the gaseous sample to a metal oxide sensor (MOS) array or pumping the gaseous sample partially into a luminol cell and partially to an MOS array;
    e. said luminol producing chemiluminescence by a chemical reaction between said luminol and said gaseous sample within said reaction cell;
    f. measuring means comprising photomultiplier tube or photodiode array for measuring the intensity of chemiluminescence and for outputting a first electrical signal indicative of the amount of explosive detected;
    g. a reduced quantity of said gaseous sample configured to be pumped to said metal oxide sensor array to prevent saturation of metal oxide detector;
    h. the MOS array comprising a conductivity sensor having a thin ceramic or fused silica sheet with an oxide sensing layer or oxide film and electrodes for measuring electrical resistance of the oxide sensing layer or oxide film, said electrical resistance being changed by adsorption of said pumped gaseous sample indicating the presence of said explosive;
    whereby the chemiluminescence measurement is refined by the metal oxide sensor measurement to eliminate the interference composition from detection.

2. The system for screening for the presence of explosives as recited by claim 1, wherein said explosive is a nitrogen free explosive, the pyrolysis of which releases $CO/CO_2$.

3. The system for screening for the presence of explosives as recited by claim 1, wherein said metal oxide sensor array includes metal oxide sensors for detecting $NO_2$.

4. The system for screening for the presence of explosives as recited by claim 1, wherein the resistance of said metal oxide sensor increases when exposed to a gaseous sample containing oxidized $NO_2$.

5. The system for screening for the presence of explosives as recited by claim 1, wherein the resistance of said metal oxide sensor decreases when exposed to a gaseous sample containing reduced $CO/CO_2$.

6. A system as recited by claim 1, wherein said metal oxide sensor is made by coating a thin sheet of ceramic or a thin sheet of fused silica onto the underside with a nickel or nickel chromium electrode heater having the top surface coated with sensing metal oxide film.

7. A system as recited by claim 6, wherein said metal oxide sensor is operated at a temperature range of 300 to 800° C.

8. A system as recited by claim 6, wherein said metal oxide sensor is operated at a temperature of 700° C.

9. A system as recited by claim 6, wherein said metal oxide film is a member selected from the group consisting of tin oxide, indium tin oxide, and tungsten oxide semiconductor.

10. A system for screening for the presence of nitrogen containing explosives, the system comprising:
    a. a chamber for collecting explosive residues;
    b. a desorber;
    c. a pyrolysis tube for pyrolyzing said explosive residue to generate a gaseous sample from decomposition of the explosive residues comprising $NO_2$;
    d. a pump for pumping the gaseous sample to a metal oxide sensor (MOS) array;
    e. a metering valve for reducing the quantity of said gaseous sample to said metal oxide sensor array, to prevent saturation of metal oxide detector;
    f. the MOS array comprising a conductivity sensor having a thin ceramic sheet or fused silica sheet with an oxide sensing layer or oxide film and electrodes for measuring electrical resistance of the oxide sensing layer or oxide film, said electrical resistance being changed by adsorption of said pumped gaseous sample indicating the presence of said explosive.

* * * * *